United States Patent
Zhu et al.

[11] Patent Number: 5,957,938
[45] Date of Patent: Sep. 28, 1999

[54] TISSUE EVERTING NEEDLE

[75] Inventors: Yong Hua Zhu; Wolff M. Kirsch, both of Redlands, Calif.; Robert B. Cushman, Cedar Crest, N.Mex.; Frank C. Maffei, Shelton, Conn.

[73] Assignee: United States Surgical Corporation, Norwalk, Conn.

[21] Appl. No.: 08/974,407

[22] Filed: Nov. 19, 1997

Related U.S. Application Data

[60] Provisional application No. 60/037,818, Feb. 5, 1997.

[51] Int. Cl.$^6$ ................................................ A61B 17/04
[52] U.S. Cl. ................................. 606/149; 606/222
[58] Field of Search ................................ 606/222, 147, 606/149

[56] References Cited

U.S. PATENT DOCUMENTS

| | | |
|---|---|---|
| 3,040,748 | 6/1962 | Klein et al. . |
| 3,908,662 | 9/1975 | Razgulov et al. ............... 606/149 |
| 4,256,251 | 3/1981 | Moskofsky . |
| 4,470,415 | 9/1984 | Wozniak . |
| 4,622,970 | 11/1986 | Wozniak . |
| 4,929,240 | 5/1990 | Kirsch et al. ................... 606/151 |
| 4,950,281 | 8/1990 | Kirsch et al. ................... 606/207 |
| 5,059,207 | 10/1991 | Shah ................................ 606/223 |
| 5,122,150 | 6/1992 | Puig ................................ 606/142 |
| 5,156,609 | 10/1992 | Nakao et al. ................... 606/142 |
| 5,300,065 | 4/1994 | Anderson ......................... 606/13 |
| 5,468,251 | 11/1995 | Buelna ............................. 606/222 |
| 5,486,187 | 1/1996 | Schenck . |
| 5,520,704 | 5/1996 | Castro et al. . |
| 5,527,324 | 6/1996 | Krantz et al. ................... 606/155 |
| 5,653,717 | 8/1997 | Ko et al. ......................... 606/147 |
| 5,720,756 | 2/1998 | Green et al. . |

*Primary Examiner*—Gary Jackson

[57] ABSTRACT

A needle for everting body tissue is a linear member having a back portion, an arcuate tissue penetrating portion, and a generally U-shaped tissue everting portion therebetween. The U-shaped tissue everting portion includes a base and first and second tissue abutment arms, the back portion preferably being collinear with the first arm and oriented at an angle with respect to the base. The needle can be incorporated into an instrument for use in endoscopic procedures. In such instruments the needle can be attached in a fixed position with respect to the instrument, or retractable within a tubular sleeve.

20 Claims, 5 Drawing Sheets

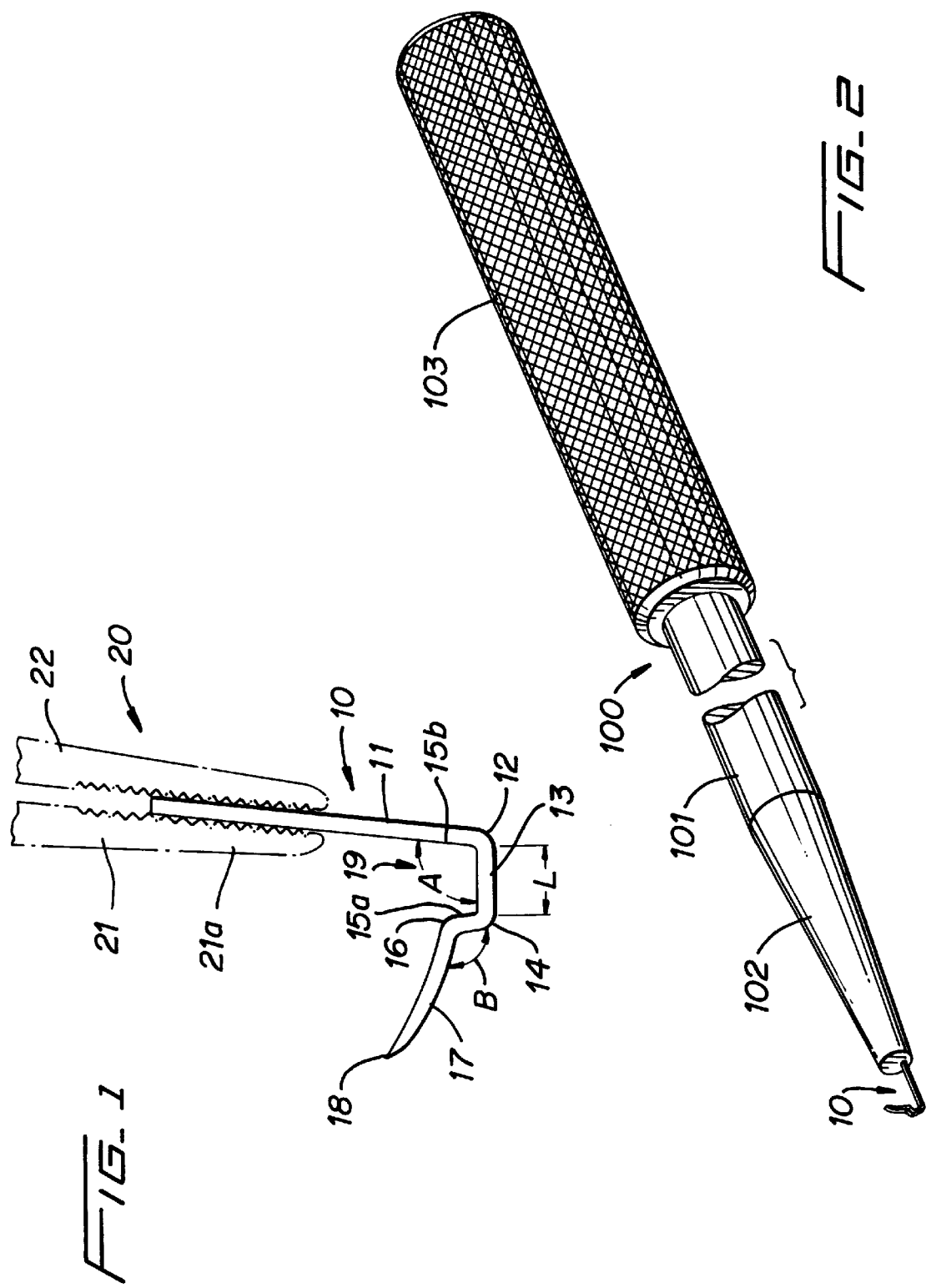

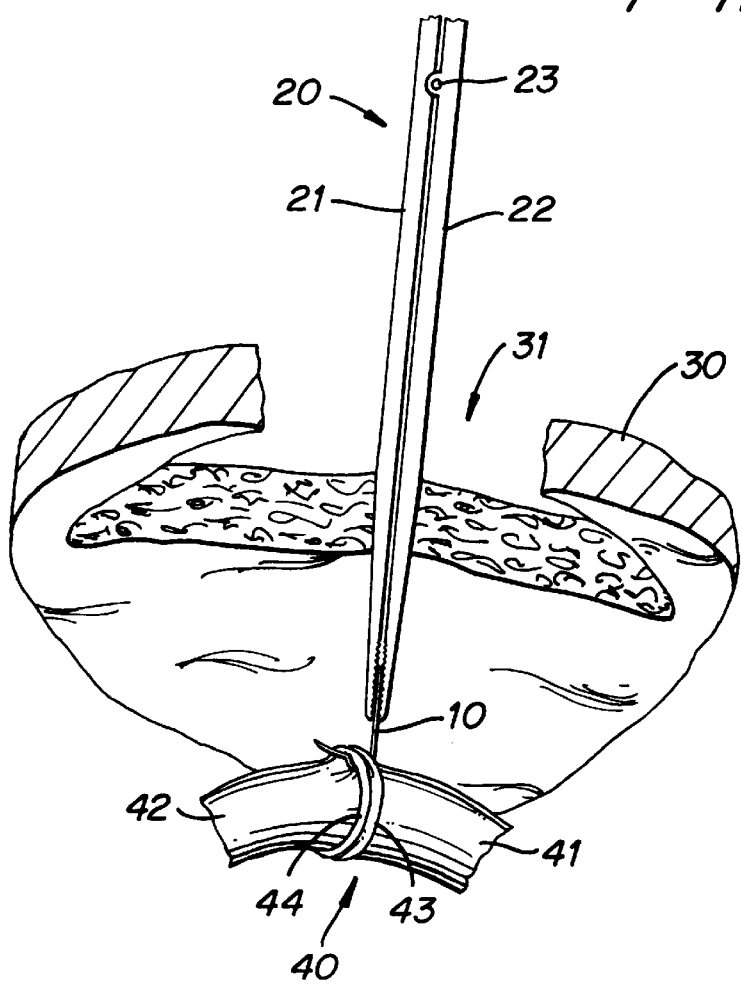
FIG_1A
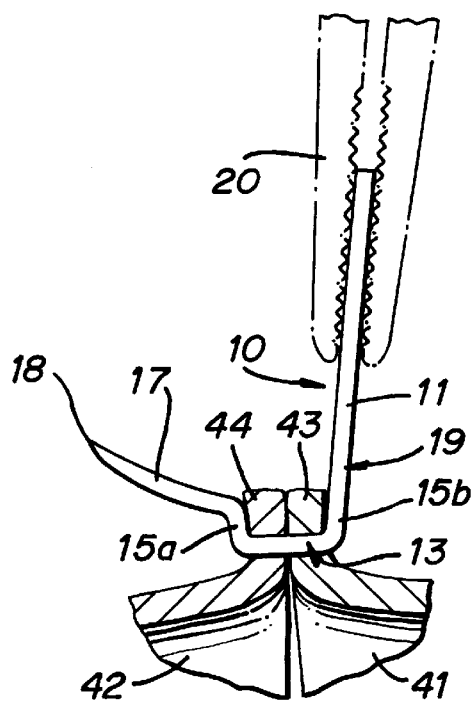
FIG_1B

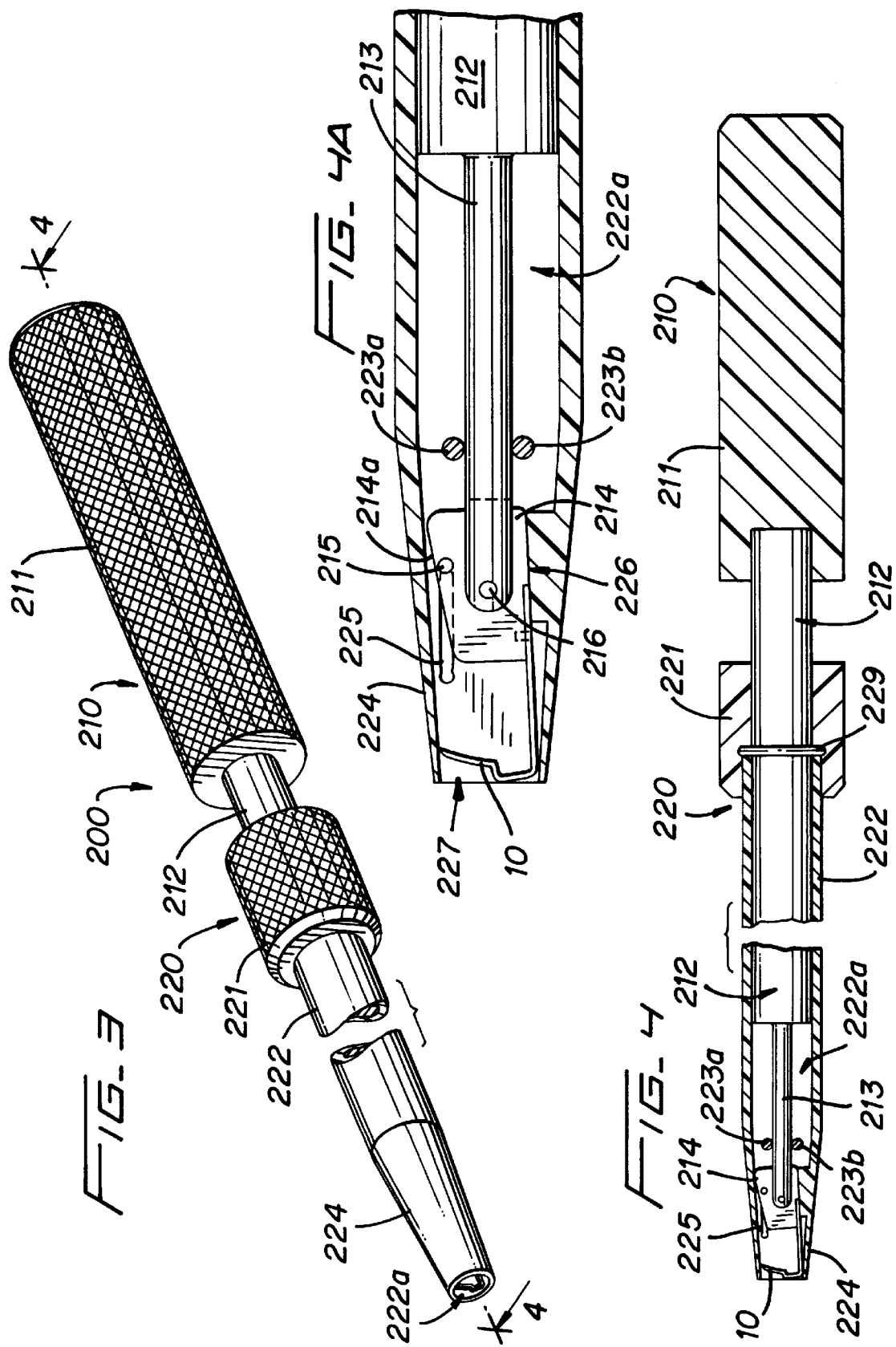

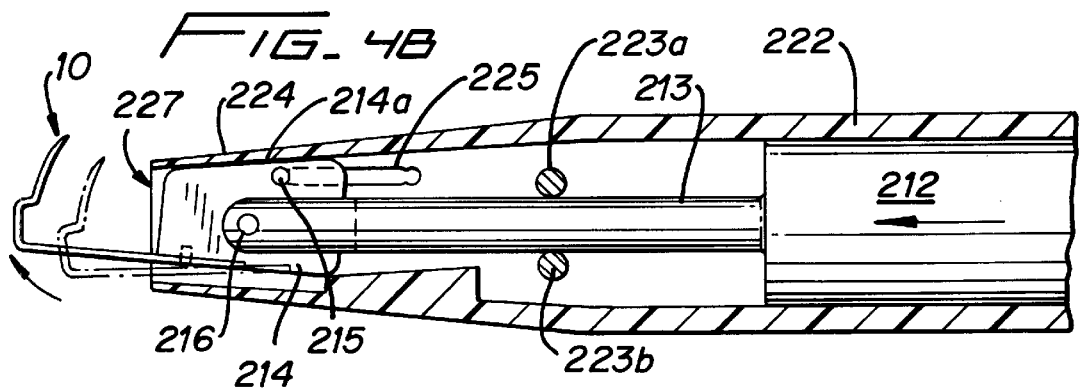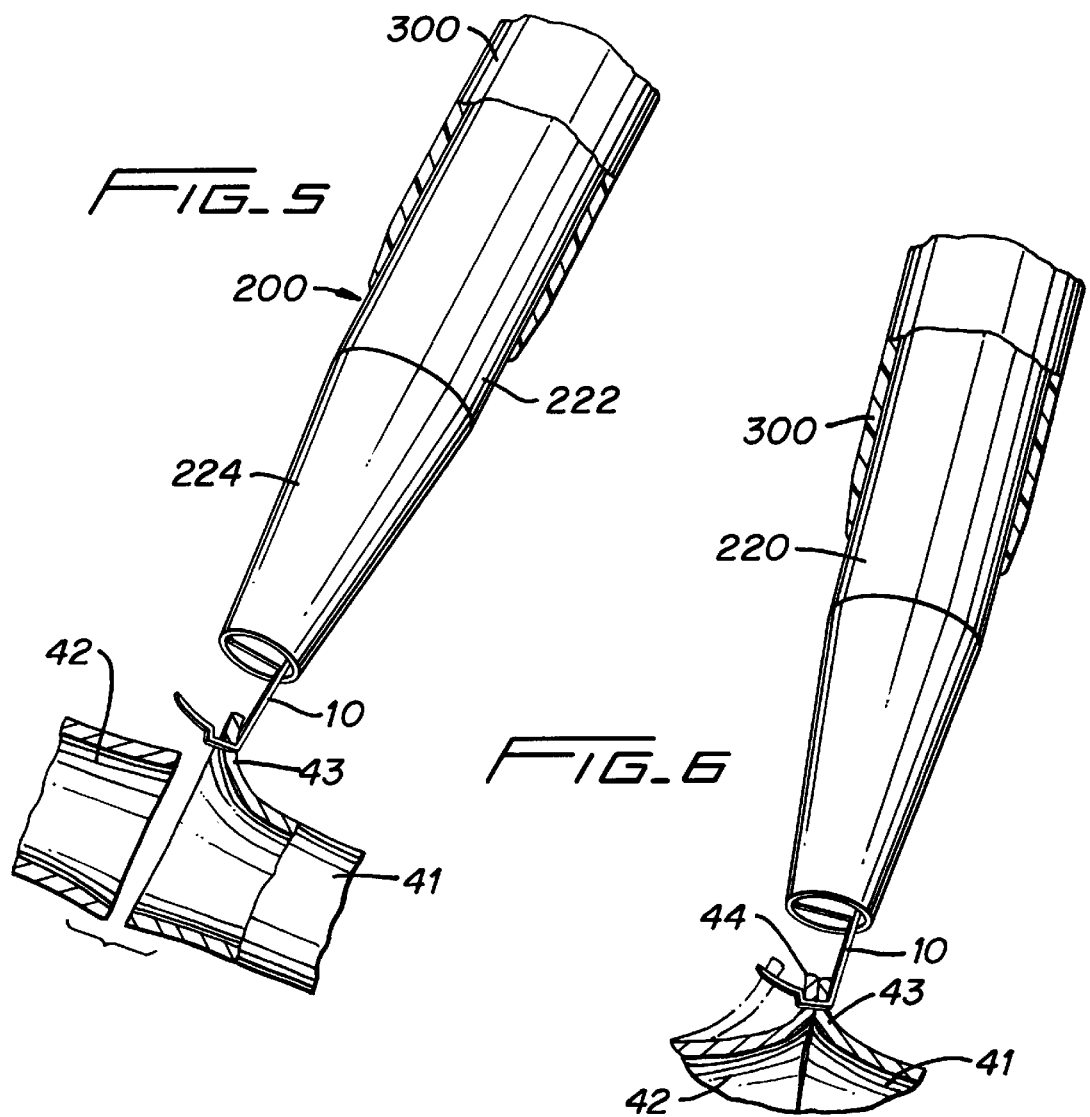

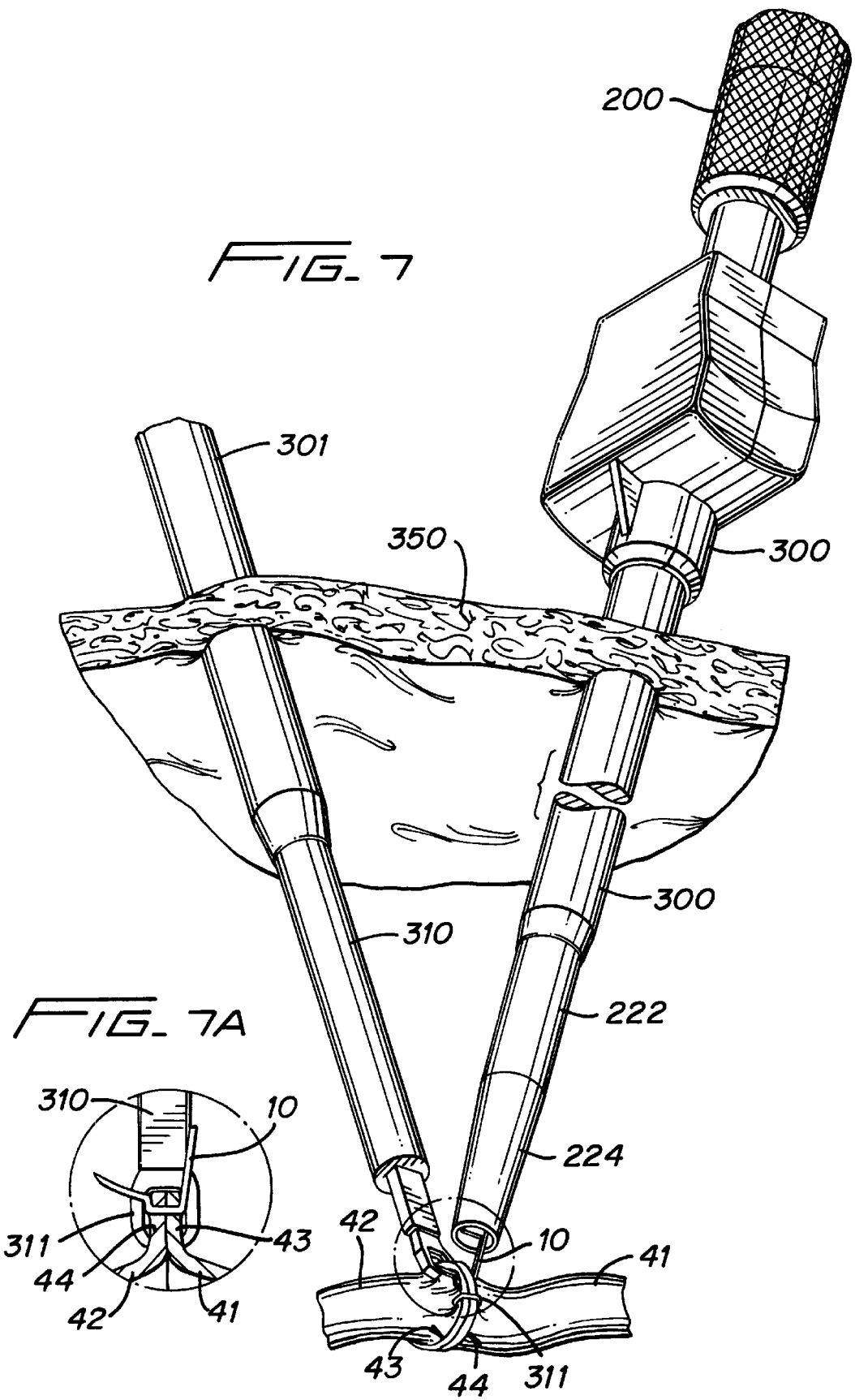

TISSUE EVERTING NEEDLE

This application claims benefit of U.S.C. Provisional application Ser. No. 60/037,818 filed Feb. 5, 1997.

BACKGROUND

1. Technical Field

The present disclosure relates to a surgical needle, particularly a needle for use in surgery which can evert body tissue to facilitate joining the ends.

2. Background of the Art

In surgical procedures for edge to edge joining of body tissue, the edges of the tissue are, often everted and held in close approximation in order for the tissue to be sutured. For example, to join the ends of tubular structures is such as blood vessels, the ends of the blood vessels can be everted to facilitate joining by suture threads. Other methods of joining such as side-to-side and end-to-side can also be used for joining tubular structures. U.S. patent application Serial No. 08/713,771, filed Sep. 12, 1996 discloses a surgical instrument for applying clips to the everted vessel portions. These non-tissue penetrating clips cause less trauma to the body tissue than suturing or penetrating clips reduce surgery tissue. Such clips require proper eversion of the body tissue.

Everting instruments are known in the art. For example, U.S. Pat. No. 5,300,065 to Anderson discloses a method and apparatus for holding and sealing a longitudinally extending edge of tissue. The tissue is everted and held in position by a clamping member.

U.S. Pat. No. 5,527,324 to Krantz et al. discloses a surgical stent for use in supporting the walls of a tubular organ during anastomosis. The stent includes a circumferential ridge adapted to evert the edges of the tubular organ to facilitate suturing.

U.S. Pat. No. 4,622,970 to Wozniak discloses a vascular everting instrument having an annular member with an iris-diaphragm mechanism to flare the leading edge of the blood vessel to facilitate anastomosis.

U.S. Pat. No. 5,486,187 to Schenck discloses a method and device for anastomosis of blood vessels. The device includes a ring-like member through which the ends of a first vessel is extended and everted back over. A second vessel end is drawn over the everted first vessel end. Fasteners are then applied to impale the vessel ends and secure them in apposition.

U.S. Pat. No. 5,520 to Castro et al. and U.S. Pat. No. 4,950,281 to Kirsch et al. disclose everting forceps which include first and second outer resilient legs interconnected at one end, and a third leg intermediate the pair of outer legs. The outer legs terminate at tips provided with arcuate jaws. The intermediate leg terminates in a spherical tip.

It would be advantageous to provide a simpler way to evert tissue and hold it in an everted configuration, especially for the application of non-penetrating clips.

SUMMARY

A needle for everting body tissue is provided herein, the needle comprising a back portion, an arcuate tissue penetrating portion, and a generally U-shaped tissue everting portion therebetween. Preferably, the needle is generally J-shaped in structure. The U-shaped tissue everting portion is preferably defined by a base and first and second tissue stop portions, the back portion preferably being collinear with the first tissue stop portion and oriented at an angle of from about 90° to about 100° with respect to the base. Also provided herein are tissue everting instruments which incorporate the aforementioned needle, and which are usable in endoscopic procedures. In one embodiment the instrument has an elongated body of such diameter as to be able to fit through a cannula, the needle being mounted to the distal end of the body. In another endoscopic embodiment the instrument includes an outer tube portion and a shaft portion. The outer tube has a tapered distal end. The needle is mounted to a pivotable plate at the distal end of the shaft portion, which is slidably disposed within the bore of the outer tube such that the needle is movable between a proximal first position within the bore of the outer tube and a distal second position outside the bore of the tube. The needle can be moved in an arcuate path to facilitate the hooking and eversion of tissue segments.

BRIEF DESCRIPTION OF THE DRAWINGS

FIG. 1 is a side elevational view of the tissue everting needle.

FIGS. 1A and 1B are side views illustrating use of the everting needle to evert vascular tissue.

FIG. 2 is a perspective view of a first embodiment of a tissue everting tool.

FIG. 3 is a perspective view of an alternative embodiment of a tissue everting tool.

FIG. 4 is a sectional side view of the embodiment of FIG. 3.

FIGS. 4A and 4B are sectional side views of the embodiment of FIG. 3 with the everting needle in proximal (retracted) and distal deployed positions, respectively.

FIGS. 5 and 6 are perspective views illustrating use of the tissue everting tool to evert tissue.

FIGS. 7 and 7A are, respectively, perspective and partly sectional side views illustrating eversion of vascular tissue in an endoscopic procedure.

DETAILED DESCRIPTION OF PREFERRED EMBODIMENTS

Referring now to FIG. 1 an everting needle 10 is shown being releasably held in the jaws of a grasping instrument 20.

The everting needle 10 is preferably a single piece structure having a back portion 11, a generally U-shaped tissue catch portion 19 having tissue abutting sides 15a and 15b, and a forward tissue penetrating portion 17. Preferably, the everting needle 10 is generally J-shaped in structure. While the description below is directed to everting the end portions of a blood vessel, it should be realized that any type of tissue, whether flat or tubular in structure can be everted by the apparatus described herein, and applicability of the apparatus for everting tissue is not limited to blood vessels. Also, eversion is contemplated for end-to-end, end to side, and side-to-side connections between tissue.

The forward tissue penetrating portion 17 is preferably curved and terminates in a sharp distal point 18. At its other end the forward tissue penetrating portion 17 is connected at bend 16 to a straight tissue stop portion 15a. Bend 16 is characterized by an angle B ranging from about 110° to about 130°. Tissue stop portion 15a is connected to a hooking base 13 at bend 14. The size and configuration of everting needle 10 is chosen such that length L of hooking base 13 is at least approximately equal to the sum of the thicknesses of the tissue layers to be everted.

Hooking base 13 is connected to tissue stop portion 15b at bend 12. Bend 12 is preferably angled at angle A, wherein angle A ranges from about 90° to about 100° and most preferably about 95°. The tissue stop portion 15a, bend 14, hooking base 13, bend 12, and tissue stop portion 15b at least partially define a generally U-shaped tissue catch portion 19. Back portion 11 extends collinearly from tissue stop portion 15b.

Referring now to FIGS. 1 and 1A, grasper 20 is a conventional pincer-like instrument having jaws 21 and 22 which are pivotally connected at pivot point 23 so as to open and close relative to each other. Jaws 21 and 22 optionally each include a serrated portion 21a and 22b, respectively, to facilitate a frictionally secure holding of the back portion 11 of the needle 10.

FIGS. 1A and 1B illustrate end-to-end eversion of two vascular tissue segments. As shown in FIG. 1A and, in more detail in FIG. 1B, everting needle 10, which is held between jaws 21 and 22 of grasper 20, is inserted through an opening 31 in a wall of body tissue 30 to gain access to divided blood vessel 40. The tissue penetrating portion 17 of the needle 10 is inserted in the vicinity of one end of vascular segment 41 from the outside of the blood vessel wall to the inside, and then through the other vascular segment 42 from the inside to the outside of the blood vessel wall. The end portions of the vascular segments 41 and 42 are moved into the tissue catch portion 19. As can be readily understood, a torque, or bending force, is exerted upon the blood vessel segments 41, 42 by needle 10 as it is maneuvered through the vessel walls to evert the end portions of the vascular segments 41, 42 into radially extending flange-like structures 43, 44, respectively, wherein the inner surfaces of the segments come into contact with each other. That is upward traction forces the tissue onto hooking base 13, causing eversion. Such contact facilitates fusion of the two segments during healing as the tissues join during regrowth. Clips such as those described in U.S. application Ser. No. 08/527,698 filed Sep. 13, 1995, and herein incorporated by reference, can be applied (using the applier disclosed in that application) to the everted portion of the tissue below the puncture made by the everting hook so that the punctured portion of the tissue remains outside the area joined together. The clips themselves are non-penetrating and hold the tissue with minimal trauma to the area of tissue joined by healing. At least in part for these reasons, this fastening technique, which is facilitated by the everting needle described herein, advantageously provides a more secure juncture of tissue.

Referring now to FIG. 2, one embodiment of a tissue everting tool which can be used in open or endoscopic procedures is designated by reference numeral 100 and includes a knurled handle portion 103, a shaft 101 which includes a tapered distal end portion 102, and an everting needle 10 (similar to that shown in FIG. 1) fixedly secured to the distal end of the shaft 101. Alternatively, needle 10 can be removably attached to the distal end of shaft 101 and replaceable with a needle of the same or different size or configuration.

As noted, tissue everting tool 100 can be used in conjunction with a cannula (not shown) in minimally invasive surgical procedures such as laparoscopic or endoscopic procedures. Typically, in such procedures a cannula is placed in an opening in a wall of body tissue and the surgical instrumentation is inserted through the cannula into the patient's body wherein the operation is performed. The opening is initially made by a sharp pointed obturator disposed through the cannula and subsequently removed leaving the cannula in place. One or more additional cannulas provide access for fiberoptic viewing instruments and other surgical instrumentation. The operating end portion of the instruments is generally long and narrow to be able to fit through the cannula and reach the inside of the body cavity where the operation is being performed. In operations such as laparoscopy wherein the operating site is insufflated, there is a gaseous seal within the instruments and between the instruments and the cannula to prevent the entry or egress of body fluids or other matter into or out from the patient's body. An advantage of minimally invasive surgery is that there is much less trauma to the patient. Both operating time and recovery time are significantly shortened. While minimally invasive surgery encompasses various different techniques, for example, laparoscopic, endoscopic, and arthroscopic techniques, the term "endoscopic" is used herein generally to mean "minimally invasive" and encompasses laparoscopic, arthroscopic, and any other minimally invasive techniques as well.

Referring now to the alternate embodiment of FIGS. 3, 4, and 4A an endoscopic tool 200 with a needle for everting vascular (or other type) tissue is shown. In this embodiment the needle 10 is retractable and is similar to the needle as shown in FIGS. 1 and 2.

More particularly, the endoscopic everting tool 200 includes a shaft portion 210 and a guide portion 220 engaged therewith. The shaft portion 210 includes a knurled handle 211, an elongated plunger 212 extending axially from the handle, a rod 213 extending axially from the plunger 212, and a needle mounting plate 214 pivotally attached to the distal end of the rod 213. Needle 10 is fixedly attached to the is mounting plate 214 and extends distally therefrom. Alternatively, needle 10 can be removably mounted to mounting plate 214 and replaceable with another needle of the same or different size or configuration.

Guide portion 220 includes a knurled handle 221 and a tubular portion 222 having a tapered distal end portion 224. Optionally, an O-ring 229 or other type gasket may be included to provide an internal gaseous seal between plunger 212.

The shaft portion 210 and guide portion 220 are assembled such that the plunger 212, rod 213 and mounting plate 214 are slidably disposed within bore 222a of the tubular portion 222. The outer diameter of plunger 212 and the inner diameter of bore 222a are close fitting so as to establish an effective seal between them. Optionally, a sealing lubricant such as a viscous biocompatible silicone grease may be employed between the plunger 212 and the inner surface of bore 222a to help maintain the gaseous seal.

Rod 213 extends between two or more guide posts. 223a and 223b, which extend laterally across bore 222a between the inner wall surfaces. Guide posts 223a and 223b are affixed to the inner wall surfaces of bore 222a and can be an integral part of the guide portion 220.

Mounting plate 214 is pivotally attached to rod 213 by pivot pin 216. Guide pin 215 extends through the mounting plate 214 and into longitudinally extending slot 225 in the tubular portion 222. The upper edge 214a of the mounting plate 214 is inclined so as to present a camming surface as the mounting plate 214 slides along an inclined bottom support surface 226.

Referring also now to FIG. 4B, as the mounting plate is distally advanced by moving handle 210 distally to advance plunger 212, everting needle 10 is moved outside exit opening 227. The upper inclined surface 214a of the mounting plate contacts and cams against the inner bore surface of the tapered portion 224 of the tubular portion 222. This camming action causes pivoting of the mounting plate at pin 216. The orientation of the mounting plate 214 is stabilized by pin 215, which rides in slot 225. The pivoting of the mounting plate 214 as it moves out causes the needle 10 to move in an arcuate hooking type action to facilitate capture and hooking of body tissue. The needle 10 can be retracted by proximal withdrawal of the shaft portion 210.

In an alternate embodiment, the mounting plate has a slot and a pivot pin is connected to the rod such that movement of the rod causes the mounting plate to pivot as the pin slides in the slot.

FIGS. 5, 6, and 7 illustrate the capture, everting, and fastening of tissue in an endoscopic procedure in end-to-end fashion. The endoscopic everting apparatus 200 is used in conjunction with a trocar cannula such as is commonly used in endoscopic procedures to create and maintain an opening in a wall of body tissue 350. Trocar cannulas suitable for use in endoscopic procedures are described in U.S. Pat. Nos. 5,030,206 and 5,127,909, for example. The trocar cannula has a gaseous sealing means to prevent egress or entry of gas or other fluids. The outer diameter of the tubular portion 222 is adapted to fit closely to the inner diameter of the cannula 300. Another cannula 301 is shown in which an endoscopic clip applying apparatus 310 is slidably disposed. Suitable endoscopic clip applying apparatus are known in the art.

As explained above, the everting needle 10 is inserted in the vicinity of one end of the vascular segments 41 from the outside to the inside of the blood vessel wall, then through the other vascular segment 42 from the inside to the outside, thereby forming flange-like structures 43 and 44.

Referring to FIGS. 7 and 7A, non-penetrating clips 311 (see e.g. aforementioned application Ser. No. 08/527,698) can now be applied to the flange-like structures 43, 44. The point at which the clip ends contact and seal the blood vessel tissue is preferably below the point at which the everting needle penetrates the tissue. A number of clips are then applied to the flange-like structures 43, 44 until the blood vessels are joined in a non-leaking connection. After a period of time the natural healing of the blood vessels 41 and 42 will cause them to join at their juncture.

The clips optionally can be fabricated from bioabsorbable material, which precludes the necessity for their removal. Clips made from a bioabsorbable synthetic polymer, such as polymers of glycolide, lactide, p-dioxanone, caprolactone, and/or trimethylene carbonate, will gradually degrade by hydrolytic attack within a few months, by which time the juncture of blood vessels will have healed.

The everting needles and clips can also be used to attach synthetic grafts to tissue.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A needle for everting body tissue which comprises:
    a substantially U-shaped portion defined by a base and first and second tissue stop portions extending from the base, a back portion extending from the first tissue stop portion, and an arcuate tissue penetrating portion extending at an angle to the second tissue stop portion.

2. The needle of claim 1 wherein the back portion is collinear with the first tissue stop portion.

3. The needle of claim 1 wherein the base and the first tissue stop portion are connected at a second bend region characterized by an angle of from about 90° to about 100°.

4. The needle of claim 1 wherein the first and second tissue stops extend at an angle to the base portion.

5. A needle for everting body tissue which comprises:
    a substantially U-shaped portion defined by a base and first and second tissue stop portions extending from the base, a back portion extending from the first tissue stop portion, and a tissue penetrating portion extending at an angle to the second tissue stop portion, wherein the tissue penetrating portion is connected to the second tissue stop portion at a first bend region characterized by an angle of from about 110° to about 130°.

6. A surgical needle having a support shaft, an arcuate tissue penetrating tip and a hook for everting body tissue, wherein the hook comprises a U-shaped portion having tissue abutting sides wherein the arcuate tissue penetrating tip extends from an end of the u-shape portion so as to define an angled bend.

7. A surgical needle comprising a generally J-shaped linear member having a linear back portion, an arcuate tissue penetrating portion, and a U-shaped tissue everting portion between the back portion and the tissue penetrating portion wherein the arcuate tissue penetrating tip extends from an end of the u-shape tissue everting portion so as to define an angled bend.

8. The surgical needle of claim 7 wherein the U-shaped tissue everting portion is defined by a base and first and second tissue stop portions extending from said base.

9. The surgical needle of claim 8 wherein the back portion is collinear with the first tissue stop portion, and the second tissue stop portion is connected to the arcuate tissue penetration portion at a first bend region characterized by an angle of from about 110° to about 130°, and the base and the first tissue stop portion are connected at a second bend region characterized by an angle of from about 90° to about 100°.

10. A tissue everting instrument comprising an elongated body and a generally J-shaped needle operatively associated therewith, the needle having a back portion, an arcuate tissue penetrating portion and a generally U-shaped tissue everting portion between the back portion and the tissue penetrating portion.

11. The tissue everting instrument of claim 10 wherein the elongated body comprises an outer tube having an axial bore defined by an inner surface and a shaft portion slidably disposed within the axial bore and movable between a distal position and a proximal position.

12. The tissue everting instrument of claim 11 further comprising a mounting plate pivotally mounted to a distal end of the shaft portion and wherein the needle is attached to the mounting plate.

13. The tissue everting instrument of claim 12 wherein the outer tube has a tapered distal end portion.

14. The tissue everting instrument of claim 13 wherein the mounting plate has an edge camming surface which is slidingly contactable with the bore inner surface at the tapered distal end portion in response to movement of the shaft portion.

15. The tissue everting instrument of claim 14 wherein the mounting plate pivots in response to sliding contact between the edge camming surface and the bore inner surface.

16. The tissue everting instrument of claim 15 wherein the needle is moved from a position substantially within the bore of the outer tube to a position substantially exterior to the bore of the outer tube in response to movement of the shaft portion from the proximal position to the distal position.

17. The tissue everting instrument of claim 16 wherein said outer tube is dimensioned for insertion within an endoscopic trocar cannula.

18. A method for everting body tissue comprising:
a) providing a needle having a back portion, a tissue penetrating portion, and a tissue everting portion between the back portion and the tissue penetrating portion;
b) inserting the tissue penetrating portion of the needle through a first layer of body tissue from an outside surface of the first layer through an inside surface of the first layer to enable the tissue everting portion of the needle to evert an end portion of the first layer
c) inserting the tissue penetrating portion of the needle through a second layer of body tissue from the inside surface of the second layer to the outside surface of the first layer, to enable the tissue everting portion of the needle to evert an end portion of the second layer such that the inside surface of the second layer is in contact with the inside surface of the first layer.

19. The method of claim 18 further including the step of applying a tissue fastener to the everted end portions of the first and second layers to keep the respective everted end portions in close approximation.

20. The method of claim 19 wherein the step of applying a tissue fastener including the step of applying a non-tissue penetrating clip.

* * * * *